(12) United States Patent
Patel et al.

(10) Patent No.: US 10,402,981 B2
(45) Date of Patent: Sep. 3, 2019

(54) IMAGE SEGMENTATION VIA MULTI-ATLAS FUSION WITH CONTEXT LEARNING

(71) Applicant: Vanderbilt University, Nashville, TN (US)

(72) Inventors: Mayur Patel, Nashville, TN (US); Patrick Kelly, Nashville, TN (US); Miya Smith, Nashville, TN (US); Andrew Plassard, Nashville, TN (US); Bennett Landman, Brentwood, TN (US); Richard G. Abramsom, Nashville, TN (US); Zhoubing Xu, Nashville, TN (US); Benjamin K. Poulose, Nashville, TN (US); Rebeccah B. Baucom, Brentwood, TN (US); Andrew Joseph Asman, Berkeley, CA (US)

(73) Assignee: VANDERBILT UNIVERSITY, Nashville, TN (US)

( * ) Notice: Subject to any disclaimer, the term of this patent is extended or adjusted under 35 U.S.C. 154(b) by 157 days.

(21) Appl. No.: 15/540,487

(22) PCT Filed: Feb. 18, 2016

(86) PCT No.: PCT/US2016/018433
§ 371 (c)(1),
(2) Date: Jun. 28, 2017

(87) PCT Pub. No.: WO2016/134125
PCT Pub. Date: Aug. 25, 2016

(65) Prior Publication Data
US 2018/0005381 A1      Jan. 4, 2018

Related U.S. Application Data

(60) Provisional application No. 62/176,433, filed on Feb. 18, 2015.

(51) Int. Cl.
*G06K 9/00* (2006.01)
*G06T 7/162* (2017.01)
(Continued)

(52) U.S. Cl.
CPC ............ *G06T 7/162* (2017.01); *G06T 7/0014* (2013.01); *G06F 19/321* (2013.01);
(Continued)

(58) Field of Classification Search
None
See application file for complete search history.

(56) References Cited

U.S. PATENT DOCUMENTS

2007/0053589 A1    3/2007  Gering
2010/0135561 A1    6/2010  Moulik
(Continued)

FOREIGN PATENT DOCUMENTS

EP      2819093 A1    12/2014

OTHER PUBLICATIONS

Acosta et al. "Multi-atlas-based segmentation of pelvic structures from CT scans for planning in prostate cancer radiotherapy." In: Abdomen and Thoracic Imaging. Nov. 9, 2013.
(Continued)

*Primary Examiner* — Atiba O Fitzpatrick
(74) *Attorney, Agent, or Firm* — Tarolli, Sundheim, Covell & Tummino LLP

(57) ABSTRACT

Systems and methods are provided for segmenting tissue within a computed tomography (CT) scan of a region of interest into one of a plurality of tissue classes. A plurality of atlases are registered to the CT scan to produce a plurality of registered atlases. A context model representing respective likelihoods that each voxel of the CT scan is a member of each of the plurality of tissue classes is determined from the CT scan and a set of associated training data. A proper
(Continued)

subset of the plurality of registered atlases is selected according to the context model and the registered atlases. The selected proper subset of registered atlases are fused to produce a combined segmentation.

16 Claims, 2 Drawing Sheets

(51) Int. Cl.
- *G06T 7/00* (2017.01)
- *G16H 50/20* (2018.01)
- *G16H 50/50* (2018.01)
- *G06F 19/00* (2018.01)

(52) U.S. Cl.
CPC ............... *G06T 2207/10081* (2013.01); *G06T 2207/20081* (2013.01); *G06T 2207/20128* (2013.01); *G06T 2207/20221* (2013.01); *G06T 2207/30016* (2013.01); *G06T 2207/30056* (2013.01); *G06T 2207/30092* (2013.01); *G06T 2207/30101* (2013.01); *G16H 50/20* (2018.01); *G16H 50/50* (2018.01)

(56) References Cited

U.S. PATENT DOCUMENTS

| | | |
|---|---|---|
| 2013/0102877 A1 | 4/2013 | Mori et al. |
| 2014/0056501 A1* | 2/2014 | Du .................. G06T 7/174 382/131 |
| 2014/0247977 A1 | 9/2014 | Han |
| 2014/0314290 A1 | 10/2014 | Dabbah et al. |
| 2015/0248768 A1* | 9/2015 | Garnavi .............. G06T 7/10 382/180 |
| 2016/0343127 A1* | 11/2016 | Miller ................. A61B 5/055 |

OTHER PUBLICATIONS

Wang et al. "Multi-atlas segmentation with joint label fusion." In: IEEE Transactions on Pattern Analysis and Machine Intelligence. Mar. 2013.

Roy et al. "A Review on Automated Brain Tumor Detection and Segmentation from MRI of Brain." In: arXiv preprint arXiv:1312.6150. Dec. 16, 2013.

Ryser et al. "Measuring medical complexity during inpatient rehabilitation after traumatic brain injury." In: Archives of physical medicine and rehabilitation. Jun. 2005.

\* cited by examiner

IMAGE SEGMENTATION VIA MULTI-ATLAS FUSION WITH CONTEXT LEARNING

RELATED APPLICATIONS

This application claims priority to U.S. Provisional Patent Application Ser. No. 62/176,433 filed Feb. 18, 2015, the entire content of which is hereby incorporated by reference.

TECHNICAL FIELD

This invention relates to medical imaging, and more particularly, to image segmentation via multi-atlas fusion with context learning.

BACKGROUND

One alternative to manual segmentation of medical images is atlas-based segmentation, in which the segmentation of a target image is derived from already segmented atlas images. The concept of atlas-based segmentation is based on the assumption that the spatial relation between two images closely resembles the spatial relation between the respective segmentations. Therefore a deformation that spatially aligns an atlas image with the target image can be used to propagate the segmentation of the atlas image. This propagated segmentation can then be considered as an estimate of the unknown true segmentation of the target image. In many applications, multiple atlases are used rather than a single atlas and in these cases, the different segmentations are combined. Atlas-based segmentation is an automatic method that reduces or eliminates the involvement that is required of a technician.

SUMMARY OF THE INVENTION

In accordance with an aspect of the present invention, a method is provided for segmenting tissue within a computed tomography (CT) scan of a region of interest into one of a plurality of tissue classes. A plurality of atlases are registered to the CT scan to produce a plurality of registered atlases. A context model representing respective likelihoods that each voxel of the CT scan is a member of each of the plurality of tissue classes is determined from the CT scan and a set of associated training data. A proper subset of the plurality of registered atlases is selected according to the context model and the registered atlases. The selected proper subset of registered atlases are fused to produce a combined segmentation.

In accordance with another aspect of the present invention, for segmenting tissue within a computed tomography (CT) scan of a region of interest into one of a plurality of tissue classes. A plurality of atlases are registered to the CT scan to produce a plurality of registered atlases. A proper subset of the plurality of registered atlases are selected. The selected proper subset of registered atlases are fused by minimizing a total expectation of labeling error, wherein a likelihood of any given set of atlases making an error is modeled as a joint probability of the set of atlases making a segmentation error at a given voxel, to produce a combined segmentation.

In accordance with yet another aspect of the present invention, a system is provided for segmenting tissue within a computed tomography (CT) scan of a region of interest into one of a plurality of tissue classes. The system includes a processor and a non-transitory computer readable medium operatively connected to the processor and storing machine executable instructions. The instructions include a plurality of registered atlases representing the region of interest and a registration component configured to register each atlas to the CT scan to provide a registered atlas in which each voxel of the region of interest is assigned to one of the plurality of tissue classes. A context learning module is configured to generate a context model, comprising respective likelihoods that each voxel of the CT scan is a member of each of the plurality of tissue classes, from at least one feature vector extracted from the CT scan.

An iterative atlas selection is configured to select a proper subset of the plurality of registered atlases according to the context model and the registered atlases. A statistical fusion model is configured to produce a combined segmentation as a probabilistic fusion from the selected proper subset of registered atlases.

DETAILED DESCRIPTION

Segmentation of medical scans is a challenging problem, with abdominal segmentation a particularly challenging problem given the inter-subject variance of human abdomens and complex 3-D relationships among organs. Multi-atlas segmentation (MAS) provides a potentially robust solution by leveraging label atlases via image registration and statistical fusion. The inventors have determined that performance on multi-organ classification can be improved by accounting for exogenous information through Bayesian priors. In one implementation, these innovations are integrated with a joint label fusion approach to reduce the impact of correlated errors among selected atlases for each organ, and a graph cut technique is used to regularize the combined segmentation. In a study of one hundred subjects, the proposed method outperformed other comparable MAS approaches, allowing efficient segmentation of large-scale clinically acquired CT data for biomarker screening, surgical navigation, and data mining.

Figure 1:
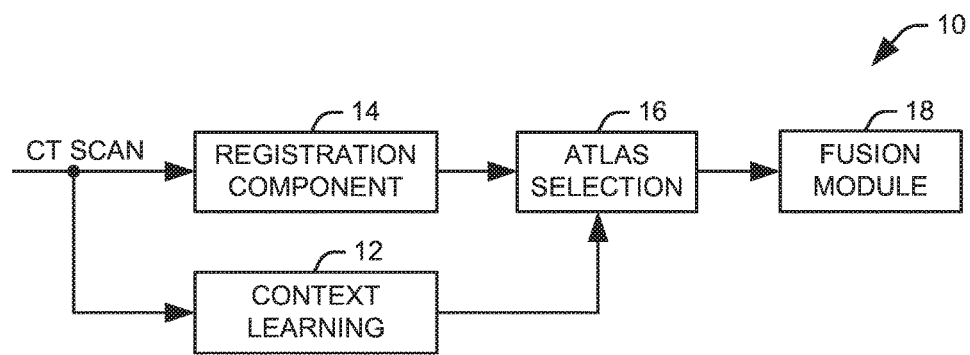
FIG. 1 illustrates one example of system for automatic segmentation of a computed tomography (CT) scan.

FIG. 1 illustrates one example of system 10 for automatic segmentation of a computed tomography (CT) scan. The system 10 includes a context learning module 12 configured to generate a context model, comprising respective likelihoods that each voxel of the CT scan is a member of each of the plurality of tissue classes, from at least one feature vector extracted from the CT scan. The context model represents the Bayesian priors for the atlas selection process discussed below. It will be appreciated that the context model is derived from the CT scan as a prior for the atlas selection, and can represent the likelihood that a given pixel belongs to a given class given only a vector of features derived from the CT scan. Examples of features can include local variance around a voxel, gradients at or near the voxel, an intensity value of the voxel, or spatial coordinates of the voxel relative to an easily identified landmark within the region of interest.

A registration component 14 is configured to register each atlas to the CT scan to provide a registered atlas in which at least a portion of a plurality of voxels in the CT scan as belonging to one of the plurality of tissue classes. Essentially, each atlas represents a verified segmentation of the region of interest in another subject or an average of a number of verified segmentations across multiple subjects. Through the registration process, the verified segmentation from each atlas is mapped onto the CT scan to provide an estimate of the segmentation of the CT scan in the form of a registered atlas.

An atlas selection component 16 is configured to select a proper subset of the plurality of registered atlases according to the context model and the registered atlases. In one implementation, an expectation maximization approach is applied using the context model as a prior. For example, each registered atlas can be compared to a weighted average of the registered atlases, and the atlases are reweighted or eliminated at each iteration according to their similarity to the average atlas. A fusion model 18 is configured to produce a combined segmentation as a probabilistic fusion from the selected proper subset of registered atlases. In one example, the statistical fusion model is configured to minimize a total expectation of labeling error, wherein a likelihood of any given set of atlases making an error is modeled as a joint probability of the set of atlases making a segmentation error at a given voxel. One example of such a process is a joint label fusion process.

Figure 2:
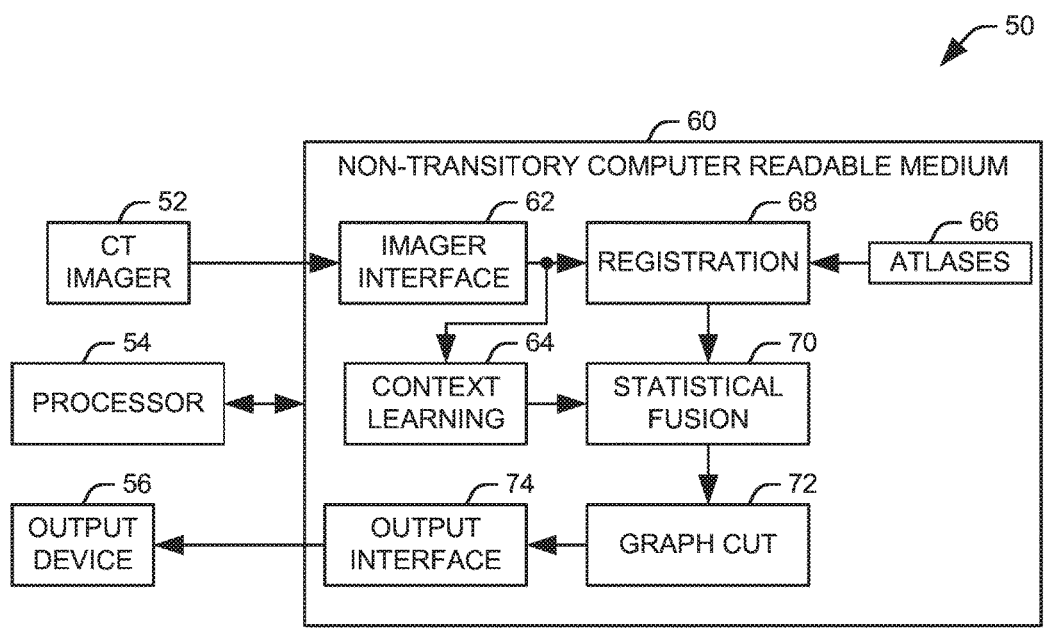
FIG. 2 illustrates an example of a system for automated segmentation of a CT scan of a human abdomen.

FIG. 2 illustrates an example of a system 50 for automated segmentation of a CT scan of a human abdomen. In the illustrated system 50, the tissues classes are individual organs within the abdomen. The system 50 includes a CT imager 52 configured to capture a CT image of at least a portion of the abdomen of a patient. The captured CT image is provided to a segmentation system, implemented as a processor 54 operatively connected to a non-transitory computer readable medium 60, at an imager interface 62. It will be appreciated that, in this example, the segmentation system is implemented as machine executable instructions, but it will be appreciated that the segmentation system could be implemented as a programmable logic gate array, other dedicated hardware, or as a mix of software instructions and dedicated hardware. The imager interface 62 is configured to format the CT scan and condition the CT scan for further processing.

The CT scan is then provided to a context learning model 64 configured to extract a probabilistic prior of the target segmentation by context learning. Specifically, the context learning model 64 generates a context model, comprising respective likelihoods for each voxel of the CT scan is a member of each of the plurality of tissue classes based on a plurality of image features extracted from the CT scan. Different classes of tissues in CT images can be characterized with multi-dimensional Gaussian mixture models using intensity and spatial "context" features. Accordingly, on a voxel-wise basis, $v \in \mathbb{R}^{d \times 1}$ represent a d dimensional feature vector, $m \in M$ indicate the tissue membership, where $M=\{1, \ldots, M\}$ is the set of possible tissues, and typically, a superset of a set of segmentation label types, L, i.e., M533L. The probability of the observed features, $\hat{v}$, given the tissue type is t can be represented with the mixture of $N_G$ Gaussian distributions, such that:

$$f(v \mid m = t) = \sum_{k=1}^{N_G} \frac{\alpha_{kt} e^{-0.5(v-\mu_{kt})^T C_{kt}^{-1}(v-\mu_{kt})}}{(2\pi)^{\frac{d}{2}} \sqrt{|C_{kt}|}} \quad \text{Eq. 1}$$

where $\alpha_{kt} \in \mathbb{R}^{1 \times 1}$, $\mu_{kt} \in \mathbb{R}^{d \times 1}$, and $C_{kt} \in \mathbb{R}^{d \times d}$ are the unknown mixture probability, mean, and covariance matrix to estimate for each Gaussian mixture component k of each tissue type t for an expectation maximization algorithm.

The context model can be trained from existing datasets with known tissue separations, for example, datasets extracted from images that have been segmented by a human expert. The tissue likelihoods on an unknown dataset, can be inferred by Bayesian expansion and can use a flat tissue membership probability from extracted feature vectors.

$$f(m = t \mid v) = \frac{f(v \mid m = t)f(m = t)}{\sum_{t'} \cdot f(v \mid m = t')f(m = t')} = \frac{f(v \mid m = t)}{\sum_{t'} f(v \mid m = t')} \quad \text{Eq. 2}$$

The segmentation system further includes a plurality of anatomical atlases 66 representing existing segmentations of the abdomen. In the illustrated implementation, each anatomical atlas is organ specific, such that the segmentation is binary, such that each voxel is labelled as either part of the organ or not part of the organ. A registration component 68 configured to register each atlas to the CT scan to provide a registered atlas in which each voxel of the region of interest is assigned to one of the plurality of tissue classes. In the instance, each registered atlas assigns each voxel of the region of interest either to a first tissue class representing its associated organ or a second tissue class representing all other tissue. It will be appreciated, however, that atlases representing more than one organ, and thus more than two tissue classes, can be employed.

An iterative atlas selection 70 is configured to select a proper subset of the plurality of anatomical atlases according to the context model and the registered atlases. In the illustrated implementation, this selection can be performed as an iterative process in which each registered atlas is compared to a weighted average of the registered atlases, and the atlases are reweighted according to their similarity to the average atlas. Atlases having low correspondence to the average are eliminated before a new weighted average is computed.

In the illustrated implementation, a non-linear rater model is used to select among the registered atlases. To this end, the latent true segmentation can be represented as a vector, $T \in L^{N \times 1}$, where $L = \{0, \ldots, L-1\}$ is the set of possible label types. In this implementation, the label types represent individual organs or structures within a human abdomen, including the spleen, the right kidney, the left kidney, the gallbladder, the esophagus, the liver, the stomach, the aorta, the pancreas, the adrenal glands, the portal and splenic veins, and the inferior vena cava. It will be appreciated, however, that the method could be used for other animals or for other regions of a human body. For example, the method can be applied to CT scans of the head to identify subregions of interest within the brain.

The registered atlases can be represented as a set of label decisions, $D \in L^{N \times R}$. For the purpose of the model, ignored, or non-selected atlases can be considered to be no better than random chance, and selected atlases can be considered to be slightly inaccurate with error factors $\varepsilon \in E^{R \times 1}$, where $$E \in \left(0, \frac{L-1}{L}\right).$$

Accordingly, the non-linear rater model, $\theta \in \mathbb{R}^{R \times 2 \times 1 \times 1}$, can be expressed as:

$$\theta_{j0s's} = \frac{1}{L}, \forall s'; \theta_{j10s's} = \begin{cases} 1 - \varepsilon_j, s' = s \\ \frac{\varepsilon_j}{L-1}, s' \neq s \end{cases} \quad \text{Eq. 3}$$

Where, j is the index of registered atlases, the second index represents a selected (1) or nonselected (0) index, s represents a true label for a tissue class, and s' represents and observed label, such that each element, $\theta_{jms's}$ represents the probability that the registered atlas, j, observes label s' given that the true label is s and the atlas selection decision is n with an error factor $\varepsilon_j$ if selected.

From the context learning, a voxel-wise a priori distribution for the underlying segmentation, $f(T_i=s)$, from the tissue likelihoods from Eq. 2. Assuming that the labels, s, of Eq. 3 correspond to the tissue types, t, of Eq. 3, $f(T_i=s) \equiv f(m=t|v)$. Given this, and retaining the notation of Eq. 3, the probability, $W_{si}^{(k)}$, that the true label associated with voxel i is label s at a $k^{th}$ iteration of the atlas selection can be expressed as:

$$W_{si}^{(k)} = \frac{f(T_i=s)\Pi_j f(D_{ij} | T_i = s, c_j^{(k)} = n, \varepsilon_j^{(k)})}{\sum_{s'} f(T_i=s')\Pi_j f(D_{ij} | T_i = s', c_j^{(k)} = n, \varepsilon_j^{(k)})} \quad \text{Eq. 4}$$

Where $c_j^{(k)}$ represents an atlas selection decision for atlas j at iteration k.

An estimation of the error factor for a next iteration, $\varepsilon_j^{(k+1)}$, can be obtained by maximizing the expected value of the conditional log likelihood of Eq. 4, such that:

$$\varepsilon_j^{(k+1)} = \underset{\varepsilon_j}{\operatorname{argmax}} \sum_i E[\ln f(D_{ij}|T_i, c_j^{(k)}, \varepsilon_j)|D, c_j^{(k)}, \varepsilon_j^{(k)}] \quad \text{Eq. 5}$$

$$= \underset{\varepsilon_j}{\operatorname{argmax}} \sum_{s'} \sum_{i:D_{ij}=s'} \sum_s W_{si}^{(k)} \ln \theta_{jc_j^{(k)}s's}$$

Accordingly, the atlas decision in the next iteration, $c_j^{(k+1)}$, can be determined as:

$$c_j^{(k+1)} = \underset{\varepsilon_j}{\operatorname{argmax}} \sum_i E[\ln f(D_{ij}|T_i, c_j^{(k)}, \varepsilon_j^{(k+1)})|D, c_j^{(k)}, \varepsilon_j^{(k+1)}] \quad \text{Eq. 6}$$

$$= \underset{c_j}{\operatorname{argmax}} \sum_{s'} \sum_{i:D_{ij}=s'} \sum_s W_{si}^{(k)} \ln \theta_{jc_js's}$$

It will be appreciated that the iterative atlas selection can be continued until a termination condition is met, such as a determination that all remaining atlases match the composite atlas, the elimination of a predetermined number of atlases, or the performance of a predetermined number of iterations.

A statistical fusion model 70 is configured to produce a combined segmentation as a probabilistic fusion from the selected proper subset of anatomical atlases. In the illustrated implementation, the statistical fusion model 70 is configured to fuse the selected proper subset of registered atlases by minimizing a total expectation of labeling error, wherein a likelihood of any given set of atlases making an error is modeled as a joint probability of the set of atlases making a segmentation error at a given voxel, to produce a combined segmentation. In one example, this can be accomplished via a joint label fusion process.

A graph cut component 72 can receive the combined segmentation from the statistical fusion model and perform a final segmentation of the region of interest. In the illustrated implementation, the atlases are specific to a given tissue structure, so the graph cut procedure can combine estimated segmentation for each of these structures and render a final segmentation representing all of the tissue structures. The resulting final segmentation can be provided to an output device 56, such as a display or a printed, via an output interface 74 to provide the final segmentation to a human operator.

It will be appreciated that this automated segmentation can be applied to any of a number of applications, including biomarker screening, surgical navigation, and research applications. In one application, a CT segmentation of the brain into a plurality of regions of interest can be utilized to predict outcomes for patients with traumatic brain injury. Once the segmentation is completed, image features, including a set of intensity characteristics, including a measure of variability (e.g., standard deviation or interquartile range) or central tendency (e.g., mean or median) across the region of interest for one or more of intensity, contrast, or similar features. Intensity features can represent a local change in the density of brain matter or pathologic intracranial abnormalities.

A second set of features is spatial features, which correspond to global shifts in spatial information such as a midline shifts or cerebral edema. A mean segmentation can be generated by calculating the spatial features by majority voting the subjects' segmented images. The number of voxels overlapping each ROI in the mean segmentation and the subject's segmentation can be used to assess global changes in structures. A set of texture features can be calculated within each ROI at distances of 1, 2, 4, and 8 mm to correspond to different levels of texture.

Once the image features have been extracted, additional features, such as biometric parameters (e.g., age, blood pressure, pulse rate, respiratory rate, etc.) and other injury metrics (Glasgow Coma Scale, Injury Severity Score, ect.) can be provided to a linear model. The linear model calculates a predicted value for one or more of predicting a patient outcome, a discharge disposition, and a length of hospital stay for a patient admitted to a hospital for a potential tramautic brain injury from the extracted features, for example, as a linear combination of the features.

Figure 3:
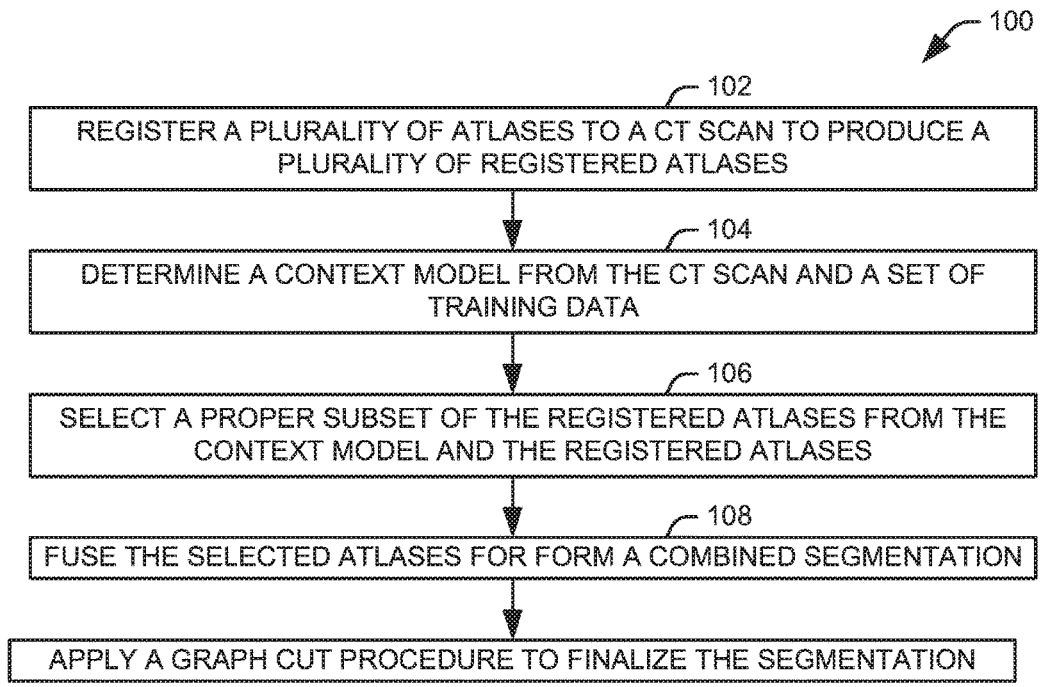
FIG. 3 illustrates a method for segmenting tissue within a CT scan of a region of interest into one of a plurality of tissue classes.

In view of the foregoing structural and functional features described above in FIGS. 1 and 2, an example method will be better appreciated with reference to FIG. 3. While, for purposes of simplicity of explanation, the method of FIG. 3 is shown and described as executing serially, it is to be understood and appreciated that the present invention is not limited by the illustrated order, as some actions could in other examples occur in different orders and/or concurrently from that shown and described herein.

FIG. 3 illustrates a method 100 for segmenting tissue within a computed tomography (CT) scan of a region of interest into one of a plurality of tissue classes. At 102, a plurality of atlases are registered to the CT scan to produce a plurality of registered atlases. Each atlas comprises a plurality of labeled voxels, indicating the membership of each voxel in one of the plurality of tissue classes, and once each atlas is registered to the CT scan, the labels associated with the atlas are mapped onto corresponding locations within the CT scan. Accordingly, the registered atlases represent labeled copies of the CT scan. In one implementation, the atlases each represent a specific tissue structure, such that only a single tissue class and a generic second tissue class representing all other tissue are included in the atlas.

At 104, a context model is determined, from the CT scan and a set of associated training data, representing respective likelihoods that each voxel of the CT scan is a member of each of the plurality of tissue classes. For example, the set of training data can be extracted from a plurality of previous verified segmentations of the region of interest. In one implementation, the context model is implemented as a Bayesian priors model. The context model can be generated by extracting a feature vector for each voxel of the CT scan and calculating a probability that each voxel belongs to a given tissue class given the extracted feature vector. In one implementation, the extracted features can include an intensity value, a gradient, a local variance, and spatial coordinates of the voxel relative to a landmark.

At 106, a proper subset of the plurality of anatomical atlases are selected according to the context model and the registered atlases. In practice, this selection can be performed as an iterative process in which each registered atlas is compared to a weighted average of the registered atlases, and the atlases are reweighted according to their similarity to the average atlas. Atlases having low correspondence to the average are eliminated before a new weighted average is computed. At 108, the selected proper subset of anatomical atlases are fused to produce a combined segmentation. In one implementation, the selected proper subset of anatomical atlases are fused by minimizing a total expectation of labeling error, wherein a likelihood of any given set of atlases making an error is modeled as a joint probability of the set of atlases making a segmentation error at a given voxel. In one example, this is accomplished via a joint label fusion model. At 110, a graph cut procedure is applied to perform a final segmentation of the region of interest. In one example, in which structure specific atlases are utilized, the graph cut procedure can be used to combine the estimated segmentation for each structure before performing the final segmentation.

Figure 4:
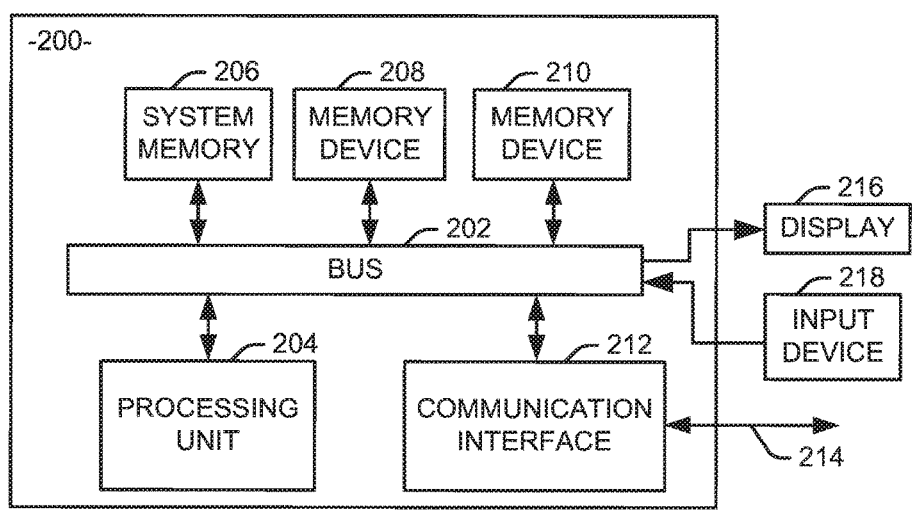
FIG. 4 is a schematic block diagram illustrating an exemplary system of hardware components capable of implementing examples of the systems and methods

FIG. 4 is a schematic block diagram illustrating an exemplary system 200 of hardware components capable of implementing examples of the systems and methods disclosed in FIGS. 1-3. The system 200 can include various systems and subsystems. The system 200 can be a personal computer, a laptop computer, a workstation, a computer system, an appliance, an application-specific integrated circuit (ASIC), a server, a server blade center, a server farm, etc.

The system 200 can includes a system bus 202, a processing unit 204, a system memory 206, memory devices 208 and 210, a communication interface 212 (e.g., a network interface), a communication link 214, a display 216 (e.g., a video screen), and an input device 218 (e.g., a keyboard and/or a mouse). The system bus 202 can be in communication with the processing unit 204 and the system memory 206. The additional memory devices 208 and 210, such as a hard disk drive, server, stand alone database, or other non-volatile memory, can also be in communication with the system bus 202. The system bus 202 interconnects the processing unit 204, the memory devices 206-210, the communication interface 212, the display 216, and the input device 218. In some examples, the system bus 202 also interconnects an additional port (not shown), such as a universal serial bus (USB) port.

The processing unit 204 can be a computing device and can include an application-specific integrated circuit (ASIC). The processing unit 204 executes a set of instructions to implement the operations of examples disclosed herein. The processing unit can include a processing core.

The additional memory devices 206, 208 and 210 can store data, programs, instructions, database queries in text or compiled form, and any other information that can be needed to operate a computer. The memories 206, 208 and 210 can be implemented as computer-readable media (integrated or removable) such as a memory card, disk drive, compact disk (CD), or server accessible over a network. In certain examples, the memories 206, 208 and 210 can comprise text, images, video, and/or audio, portions of which can be available in formats comprehensible to human beings.

Additionally or alternatively, the system 200 can access an external data source or query source through the communication interface 212, which can communicate with the system bus 202 and the communication link 214.

In operation, the system 200 can be used to implement one or more parts of an image segmentation system in accordance with the present invention. Computer executable logic for implementing the diagnostic system resides on one or more of the system memory 206, and the memory devices 208, 210 in accordance with certain examples. The processing unit 204 executes one or more computer executable instructions originating from the system memory 206 and the memory devices 208 and 210. The term "computer readable medium" as used herein refers to a medium that participates in providing instructions to the processing unit 204 for execution, and can, in practice, refer to multiple, operatively connected apparatuses for storing machine executable instructions.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications, and variations that fall within the scope of the appended claims.

What is claimed is:

1. A method for segmenting tissue within a computed tomography (CT) scan of a region of interest into one of a plurality of tissue classes, comprising:
    registering a plurality of atlases to the CT scan to produce a plurality of registered atlases, each registered atlas labelling at least a portion of a plurality of voxels in the CT scan as belonging to one of the plurality of tissue classes;
    determining, from the CT scan and a set of associated training data, a context model representing respective likelihoods that each voxel of the CT scan is a member of each of the plurality of tissue classes;
    selecting a proper subset of the plurality of registered atlases according to the context model and the registered atlases; and
    fusing the selected proper subset of registered atlases to produce a combined segmentation.

2. The method of claim 1, wherein fusing the selected proper subset of registered atlases comprises fusing the selected proper subset of registered atlases by minimizing a total expectation of labeling error, wherein a likelihood of any given set of atlases making an error is modeled as a joint probability of the set of atlases making a segmentation error at a given voxel.

3. The method of claim 2, where fusing the selected proper subset of registered atlases comprises fusing the selected proper subset of registered atlases via a joint label fusion model.

4. The method of claim 1, further comprising applying a graph cut procedure to perform a final segmentation of the region of interest.

5. The method of claim 1, wherein determining a context model comprises:
extracting a feature vector for each voxel of the CT scan representing at least one context feature of the CT scan; and
calculating a probability that each voxel belongs to a given tissue class given the extracted feature vector, the set of training data being extracted from a plurality of previous verified segmentations of the region of interest.

6. The method of claim 5, wherein calculating the probability, f(v|m=t) that each voxel belongs to a given tissue class given the extracted feature vector comprises:

$$f(v \mid m = t) = \sum_{k=1}^{N_G} \frac{\alpha_{kt} e^{-0.5(v-\mu_{kt})^T C_{kt}^{-1}(v-\mu_{kt})}}{(2\pi)^{\frac{d}{2}} \sqrt{|C_{kt}|}}$$

where $\alpha_{kt} \in \mathbb{R}^{1 \times 1}$, $\mu_{kt} \in \mathbb{R}^{d \times 1}$, and $C_{kt} \in \mathbb{R}^{d \times d}$ are the unknown mixture probability, mean, and covariance matrix to estimate for each Gaussian mixture component k of each tissue type t for an expectation maximization algorithm.

7. The method of claim 5, extracting a feature vector for each voxel of the CT scan representing at least one context feature of the CT scan comprises extracting at least two of an intensity value, a gradient, a local variance, and a spatial coordinate relative to a landmark for the voxel.

8. The method of claim 1, wherein the region of interest is a human abdomen and each of the plurality of tissue classes represents one of an organ and a blood vessel within the abdomen.

9. The method of claim 8, wherein the plurality of tissue classes comprises classes representing at least three of a spleen, a right kidney, a left kidney, a gallbladder, an esophagus, a liver, a stomach, an aorta, a pancreas, adrenal glands, portal and splenic veins, and an inferior vena cava.

10. The method of claim 1, wherein the region of interest is a human head, and the plurality of tissue classes represent subregions of interest within a brain.

11. The method of claim 10, further comprising:
extracting a set of features from each subregion of interest; and
predicting at least one of a patient outcome, a discharge disposition, and a length of hospital stay for a patient admitted to a hospital for a potential traumatic brain injury from the extracted feature sets.

12. A system for segmenting tissue within a computed tomography (CT) scan of a region of interest into one of a plurality of tissue classes, comprising:
a processor;
a non-transitory computer readable medium operatively connected to the processor and storing machine executable instructions, the instructions comprising:
a plurality of registered atlases representing the region of interest;
a registration component configured to register each atlas to the CT scan to provide a registered atlas in which at least a portion of a plurality of voxels in the CT scan as belonging to one of the plurality of tissue classes;
a context learning module configured to generate a context model, comprising respective likelihoods that each voxel of the CT scan is a member of each of the plurality of tissue classes, from at least one feature vector, comprising a plurality of image features, extracted from the CT scan;
an iterative atlas selection configured to select a proper subset of the plurality of registered atlases according to the context model and the registered atlases; and
a statistical fusion model configured to produce a combined segmentation as a probabilistic fusion from the selected proper subset of registered atlases.

13. The system of claim 12, further comprising a graph cut component to perform a final segmentation of the region of interest.

14. The system of claim 12, wherein the statistical fusion model is configured to fuse the selected proper subset of registered atlases by minimizing a total expectation of labeling error, wherein a likelihood of any given set of atlases making an error is modeled as a joint probability of the set of atlases making a segmentation error at a given voxel, to produce a combined segmentation.

15. The system of claim 14, wherein the statistical fusion model is configured to apply a joint label fusion process.

16. The system of claim 12, wherein the set of training data is extracted from a plurality of previous verified segmentations of the region of interest and the context learning model is configured to extract a feature vector for each voxel of the CT scan representing at least one context feature of the CT scan and calculate a probability that each voxel belongs to a given tissue class given the extracted feature vector.

* * * * *